United States Patent [19]

Austin et al.

[11] 4,337,654

[45] Jul. 6, 1982

[54] NATURAL GAS CALORIMETER

[75] Inventors: Robert R. Austin, Pasadena; Ernst R. Ginkel, San Dimas, both of Calif.

[73] Assignee: International Telephone and Telegraph Corporation, New York, N.Y.

[21] Appl. No.: 183,419

[22] Filed: Sep. 2, 1980

[51] Int. Cl.³ .............................................. G01K 17/04
[52] U.S. Cl. ................................................. 73/190 CV
[58] Field of Search ................ 73/190 CV, 190 R, 26; 422/51; 23/230 R, 230 PC

[56] References Cited

U.S. PATENT DOCUMENTS 4,125,123  11/1978  Clingman, Jr. ................ 73/190 CV Primary Examiner—Stephen A. Kreitman
Attorney, Agent, or Firm—A. Donald Stolzy

[57] ABSTRACT

Gross calorific content available from natural gas combustion determined from proportionality to molar oxygen demand in an apparatus including: provision for supplying gas and air at fixed, standard volumetric rates such that oxygen is present in excess; a combustion chamber employing swirled mixture introduction to effect complete gas burning; an oxygen sensor to detect deviation of combustion product oxygen content from an optimum setpoint value; an electrolytic hydrogen (oxygen) generator, the output of which adds to the gas and air mixture prior to combustion; and electronic control circuitry to maintain setpoint through regulation of an electrolysis current. Said current, or its control signal, also serves as a direct electronic meter of the generated species. Thus, through calibration, a measure of oxygen demand and calorific value is provided.

12 Claims, 7 Drawing Figures

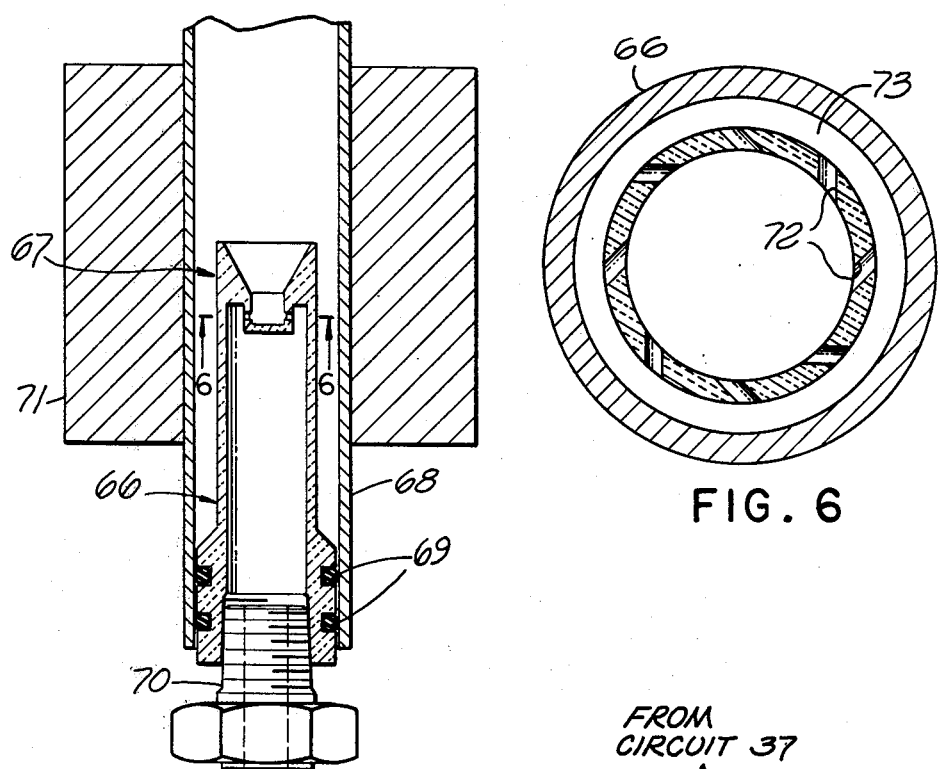
FIG. 5
FIG. 6
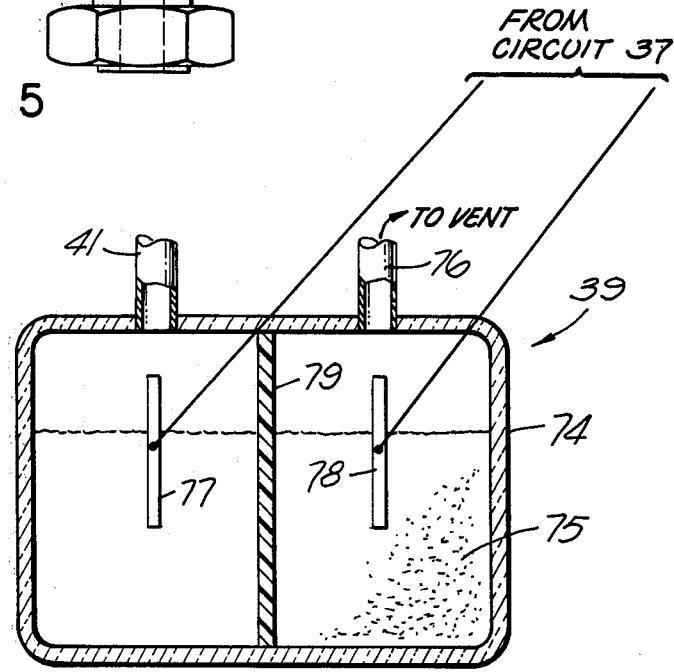
FIG. 7

NATURAL GAS CALORIMETER

BACKGROUND OF THE INVENTION

This invention relates to combustible gas calorimetry, and more particularly, to an instrument for the automatic and continuous determination of the gross heat available from the combustion of various natural gases.

PRIOR ART STATEMENT

Calorific value has been measured and recorded for many years in the natural gas industry. The previously preferred instruments have been based on principles of wide generality, and, although capable of considerable accuracy, have entailed appreciable inconvenience and expense. The traditional technique involves: bringing gas and air to a constant temperature and water vapor saturation level through contact with a water bath; separate metering of gas, combustion air and auxiliary air by means of wet test type rotary meters on a common drive shaft; effecting the combustion and transfer of heat released, both directly and through condensation of combustion product moisture, to auxiliary air; and finally, taking a precision temperature measurement.

These steps have been performed in a massive assembly of substantial heat capacity. Slow instrument response has been an unavoidable consequence of the system's reluctance to reach a new temperature equilibrium. Optimum accuracy, in the range of 0.25%, may be achieved after 40 to 60 minutes. Even performance levels approaching 0.5% have required installation in a space where precise regulation of ambient air temperature can be provided. Such a calorimeter is, thus, cumbersome and costly.

Recent developments in the art have included approaches from analytical chemistry. Relative concentrations of natural gas constituent components are determined in gas chromatographs dedicated to computing calorific content from the known contributions of the pure gases. It is not yet clear whether a high order of accuracy is likely to be sustained under field conditions. Expense associated with this technique may be only marginally less than for classical calorimetry.

See also the American Gas Association paper AGA (72-D-13) entitled "New Approach to the Continuous Measurement of Calorific Values of Gaseous Fuels", by William H. Clingman, Jr., Consultant, Precision Machine Products, Inc.

SUMMARY OF THE INVENTION

In accordance with the calorimeter of the present invention, the above-described and other disadvantages of the prior art are overcome by providing a means to determine oxygen demand for the complete combustion of natural gas. Over the range of concentrations in which saturated hydrocarbons occur in natural gas distribution and delivery systems, the gross energy released through combustion is substantially proportional to the oxygen consumed. A particular feature of the present invention resides in the determination of oxygen demand through a gas phase titration. The titration reaction is combustion. Necessary titrant is automatically and continuously generated and measured by the action of an electronic control circuit. Based upon the level of residual oxygen detected in combustion exhaust products, the output of an electrolytic generator is controllably varied so that the electrolytic titrant, when added to a volumetrically constant mixture of natural gas and air, maintains or restores the mixture to an optimal and constant oxygen excess.

An electrolytic generator construction capable of rapid, dynamic response and of minimal material cost constitutes another feature of the present invention. The electrolytically generated titrant may be either oxygen or hydrogen. The use of hydrogen to perform a back titration of an oxygen-rich mixture is to be preferred since it enhances both performance and safety.

Still another feature of the present invention resides in a burner construction providing highly stable combustion characteristics for low gas flow rates.

A further feature of the invention resides in a pneumatic diaphragm pump.

BRIEF DESCRIPTION OF THE DRAWINGS

In the accompanying drawings which illustrate exemplary embodiments of the present invention;

FIG. 5 is a vertical sectional view through a combustion chamber and a burner constructed in accordance with a feature of the present invention;

FIG. 6 is a transverse sectional view of the burner; and

FIG. 7 is a vertical sectional view, partly in elevation, of a hydrogen generator constructed in accordance with another feature of the present invention.

DESCRIPTION OF THE PREFERRED EMBODIMENTS

Figure 1:
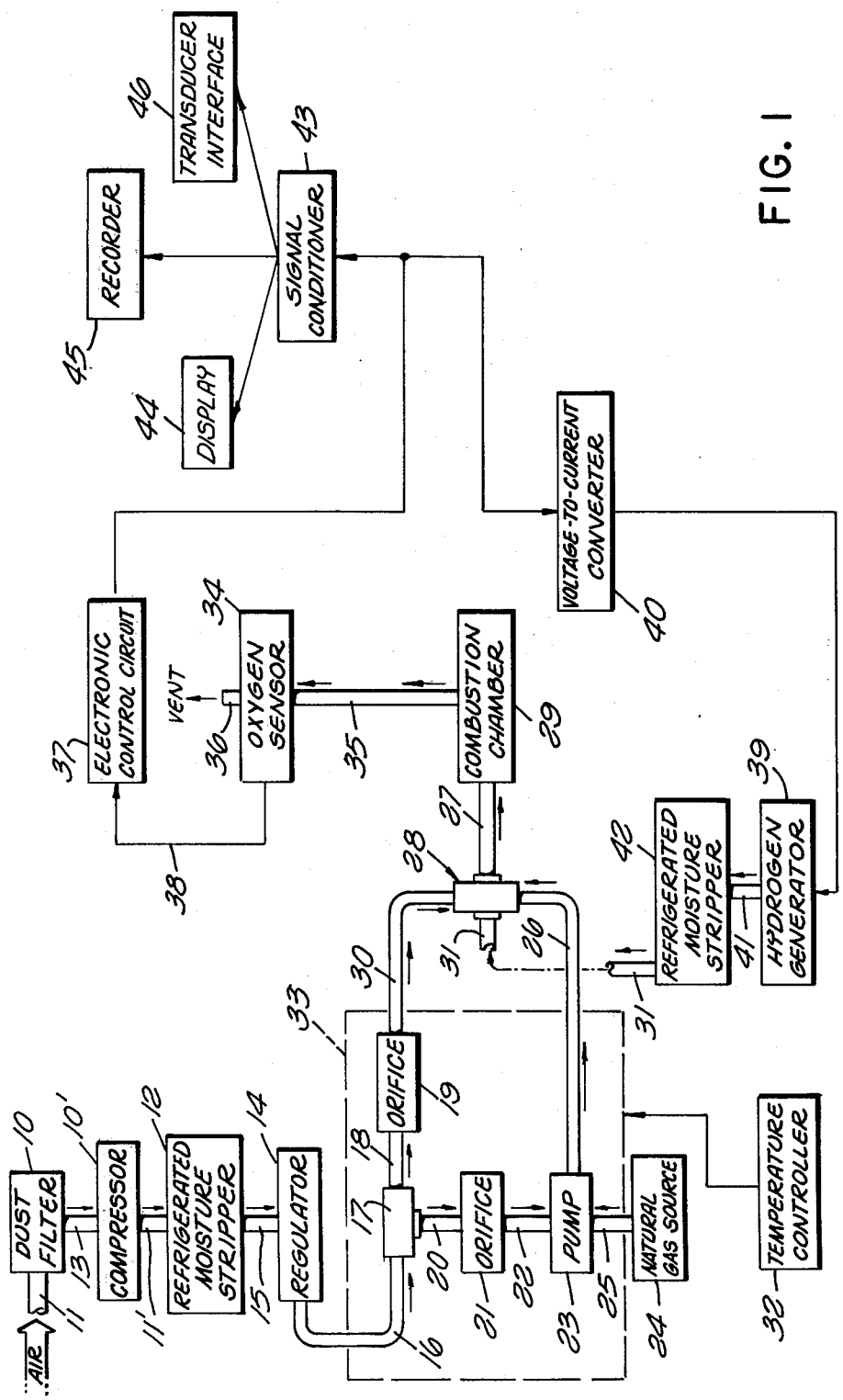
FIG. 1 is a block diagram of a calorimeter constructed in accordance with the present invention.

In FIG. 1, a calorimeter constructed in accordance with the present invention is shown, including a dust filter 10 having an inlet conduit 11 to receive ambient air from the atmosphere.

Filter 10 supplies filtered air to a refrigerated moisture stripper 12 over a conduit 13 through a compressor 10' and a conduit 11'.

Stripper 12 supplies dry air to a precision pressure regulator 14 over a conduit 15.

A conduit 16, a pipe tee 17 and a conduit 18 are connected in succession from regulator 14 to an orifice 19. The pipe tee 17 also has a conduit 20 connected therefrom to an orifice 21. Orifices 19 and 21 are sized to establish air and gas flow rates to be elaborated.

Air passes through orifice 21 and a conduit 22 to operate a pump 23. Pump 23 pumps natural gas from a source 24 through a conduit 25 and through a conduit 26 to a conduit 27 through a 4-way pipe connection 28 to a combustion chamber 29. Connection 28 receives air from orifice 19 through a conduit 30, and hydrogen gas through a conduit 31.

A temperature controller 32 provides a stable thermal environment in a housing 33 containing all flow regulating elements downstream of regulator 14: orifices 19 and 21; pump 23; as well as sufficient air and gas conduit, 16 and 25, respectively; to ensure temperature equilibrium of air and gas prior to orifice metering and pumping.

The air in conduit 30 has a volume flow rate adequate to supply oxygen in excess of that required to produce complete combustion of natural gas in conduit 26. When the calorific value of the natural gas in conduit 26 is a predetermined maximum, the excess may be about three percent. Hydrogen is supplied through conduit 31 to utilize excess oxygen. Thus, there is substantially complete combustion in chamber 29.

An oxygen sensor 34 is preferably disposed within the exhaust flue 35 of chamber 29. Conduit 36 serves to vent combustion products.

The output of oxygen sensor 34 is connected to an electronic control circuit 37 via electrical leads 38. Circuit 37 generates control signals serving to maintain or restore input from sensor 34 to a fixed setpoint level. An appropriate setpoint may correspond with an oxygen concentration of about one-half of one percent in conduit 35.

Current supplied to an electrolytic hydrogen generator 39 is governed by the magnitude of the control signal applied to a voltage-to-current converter 40. It is expedient to bias the hydrogen current supply so that a setpoint level input to circuit 37 results in a current of several hundred milliamperes when the calorific value of the natural gas is maximal. The bias may be introduced as a zero offset in either the output signal of circuit 37 or in converter 40.

Bias current ensures that a nonzero electrolysis current is supplied to generator 39 at all times. Consequently, a positive hydrogen flow rate is always supplied to conduit 41, refrigerated moisture stripper 42, and to join air and gas via conduit 31.

Elements 29, 34, 37, 39 and 42 and their interconnections will be seen to form a self-regulating feedback control system in which the degree of hydrogen generation required is an inversely proportionate measure of the oxygen demand of the gas supplied.

A signal conditioner 43 provides adjustable electrical gain and zero offset with which the titrant control signal from circuit 37 can be calibrated in terms of calorific content of natural gas per standard volumetric unit. Signal averaging may or may not be desirably incorporated in conditioner 43, depending on the details of interaction between elements in the feedback system.

Signal conditioner output may be connected to devices to display 44 and record 45 measurement results, as well as to components to interface 46 results with diverse data acquisition systems or control transducers.

All of the structures illustrated in FIG. 1 may be entirely conventional, except as indicated herein. The use of hydrogen generator 39 and some of the other structures by themselves and in combination therewith is one feature of the present invention. Another feature resides in the use of pump 23, the details of which will be supplied hereinafter. Another feature of the present invention resides in the details of the construction of combustion chamber 29, such details being described in the following.

Sensor 34 may be an oxygen level detector employing known principles. A high temperature, ceramic oxide, electro-chemical sensor with a Nernstian output may be appropriate.

Electronic control circuit 37 employs proportional band, rate and reset modes conventional to process setpoint controllers. The entire feedback control system, hence, the calorific measurement itself, attains optimum performance only through the selection of control mode parameters commensurate with the dynamic response characteristics of: hydrogen generation and delivery, mixture combustion, and oxygen sensing; in an apparatus of a given configuration.

Figure 2:
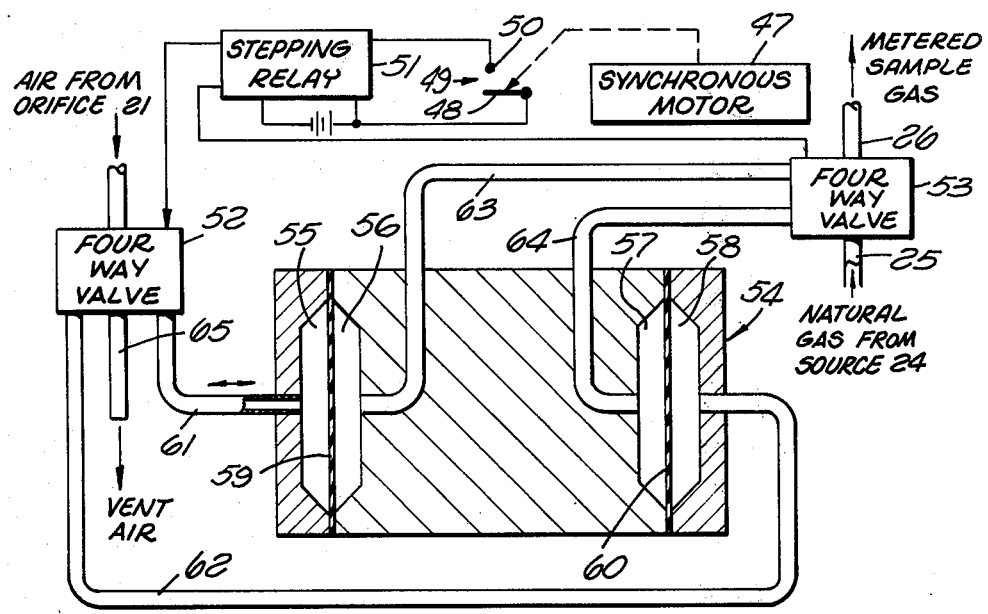
FIG. 2 is a partial schematic and transverse sectional view of a pump constructed in accordance with a feature of the present invention.

The construction and operation of a diaphragm pump 23 may be better understood with reference to FIG. 2. A synchronous motor 47 rotates a pole 48 of a switch 49. Switch 49 has a contact 50, engageable by pole 48 periodically, at a constant frequency. Engagement of pole 48 with contact 50 causes a stepping relay 51 to energize spring biased multi-way valves 52 and 53 alternately. Valve actuating means 47, 49 and 51 need not be contained within temperature controlled housing 33.

A body 54 has internal surfaces forming cavities 55, 56, 57 and 58, with diaphragms 59 and 60. Diaphragms 59 and 60 are slack at equilibrium and freely extensible throughout the greater portion of their cavities. Conduits 61 and 62 supply air to and receive air from cavities 55 and 58, respectively. Conduits 63 and 64 feed natural gas to, or receive natural gas from, cavities 56 and 57, respectively.

When, in FIG. 1, air is supplied from orifice 21 and conduit 22 via valve 52 and conduit 61 to cavity 55, air from cavity 58 is being vented at conduit 65 via conduit 62, and vice versa. Natural gas to and from cavities 56 and 57, likewise, alternate. When natural gas is being supplied to cavity 56, it is being withdrawn from cavity 57 and provided therefrom to outlet conduit 26. The reverse is thus true in the case of both air and natural gas.

Figures 3, 4:
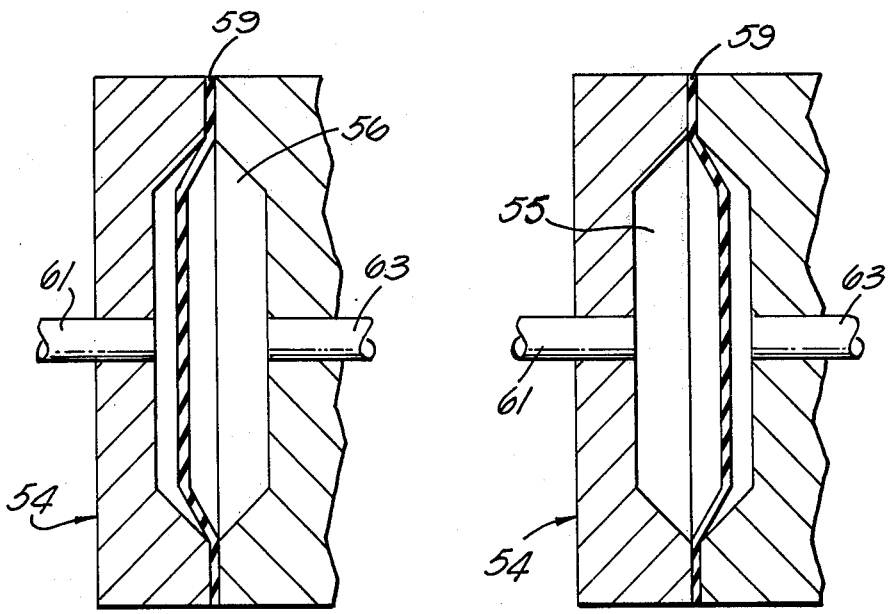
FIGS. 3 and 4 are broken-away transverse sectional views of a pump diaphragm in the two respective extreme limits of its travel.

Natural gas is supplied to valve 53 from a source 24 over a conduit 25. In FIG. 3, the supply of natural gas to cavity 56 has increased the cavity volume defined by position of diaphragm 59 and, simultaneously, vented air from the diminishment of cavity 55.

In FIG. 4, air enters conduit 61 and drives out the gas in cavity 56 into conduit 63 and outwardly of valve 53 through conduit 26. The switching frequency of timing means 47 is selected to cycle prior to the full utilization of free diaphragm travel.

In FIG. 5, a mixture delivery tube is shown at 66 with a burner head 67. An exhaust flue is provided at 68. O-ring seals are provided at 69. A fitting 70 is threaded into tube 66, fitting 70, if desired, incorporating a conventional flashback flame arrestor (not shown).

An insulating jacket is provided at 71.

In FIG. 6, note will be taken that the inner cup of burner head 67 has jet openings 72. Jet openings 72 have internal surfaces of revolution having axes, each angularly displaced from its respective radial toward the tangential, all in the same clockwise, or counterclockwise, sense. A chamber of annular cross section is provided at 73 in order for mixture to gain access to jets 72.

Materials appropriate to the construction of burner head 67 and mixture delivery tube 66 are refractory materials which are castable or machineable, for example, soapstone, which is subsequently heat treated. Flue 68 may be conveniently constructed of tubular silica.

In FIG. 7, hydrogen generator 39 is shown including a container 74 to hold an electrolyte 75, outlets for hydrogen and oxygen 41 and 76, respectively, a cathode 77 fixed relative to and inside of container 74, a similarly mounted anode 78 and a preferably non-corrodible, non-conductive partition 79.

Electrolyte 75 may be any conventional electrolyte but, preferably, is sodium hydroxide or potassium hydroxide, or other alkali metal hydroxide in an aqueous solution.

If desired, generator 39 may be any conventional generator that produces hydrogen by electrolysis.

It is important, however, that the volume of the space above the electrolyte be kept minimal, in order that generator 39 may be capable of a fast response in hydrogen delivery upon any change in current supplied to it as a result of electrical control action. For the same reason, moisture removal means 42 are to be miniaturized, and it is preferable to incorporate such means within the structure of generator 39.

While permitting necessary ion exchange, partition 79 serves to separate and isolate the gases evolved at cathode and anode, respectively, and to prevent side-to-side displacement of electrolyte which would otherwise result from changes in the pressure against which hydrogen is delivered. Separator 79 may be constructed of a suitable membrane.

DISCUSSION

Practice of the present invention comprehends four functions: (a) flow regulation; (b) combustion; (c) oxygen detection; and (d) titrant control and measurement. Considerations important to each individual function are described:

(a) The precision with which the gas' oxygen demand can be determined is dependent upon the provision of oxygen and gas at rates which remain volumetrically invariant referenced to standard conditions of pressure and temperature. In falling short of this objective, error is minimized if the ratio of oxygen to gas remains constant. To this end, the calorimeter of the present invention employs air piloted, positive displacement gas metering. The substantially unchanging composition of dry, ambient air is utilized, after regulation of temperature and pressure, to supply a pair of orifices which dispense pilot air and combustion air, respectively. The common supply pressure selected is preferably not less than twice the absolute pressure against which the orificed air is delivered. The orifices are desirably configured and operated as may be required to achieve a sonic or critical condition so that the influence of downstream conditions upon air flow rate is minimized.

Compressor 10' draws air form a pick-up 11 located out of doors, and where direct contamination, such as may be due to automotive exhaust, is avoided. Oil, or other foreign matter, is not to be introduced by the compressor. Water vapor content is then reduced to a dewpoint less than approximately 10 C., at an air pressure of not less than three atmospheres absolute. All flow-governing elements subsequent to regulator 14 are desirably maintained at a constant temperature.

(b) Attainment of a sufficient degree of repeatability and resolution requires essentially complete combustion of gas hydrocarbons to carbon dioxide and water.

The structure of FIG. 5 satisfies this requirement, bringing about substantially complete combustion of gas flowing at very low rates. Low gas flow rates promote the achievement of important objects of the present invention involving size, convenience and cost. They make electrolytic generation of adequate titrant easy to effect. An appropriate rate of gas flow is in the range of 30 to 60 ml./min.

The structure of FIG. 5 operates in a vertical orientation, with the flue 68 serving to remove combustion products from the flame region in a reliable manner while preserving the exhaust's identity prior to oxygen detection. Mixture delivery tube 66 is extended sufficiently from burner head 67 to provide a location for 0-ring mounting of flue 68, not subject to degradation due to combustion heat.

Burner head 67 has a small cupped region within the upper end of the mixture delivery tube 66. This is the flame site. The mixture enters the cup through the plurality of small sidewall holes 72 communicating between the cup and the annular chamber 73. Angular orientation of the jets imparts a uniformly high tangential or swirl motion to the mixture upon entering the cup. A nozzle-like configuration directs the products of combustion upward in making the transition from cup to flue. Fabrication of the burner head 74 as an integral part of the mixture delivery tube 73 eliminates the need for an additional sealing joint.

(c) Oxygen sensor 34 continouously provides an input signal to hydrogen control circuit 37. According to the present invention, the absolute accuracy and rangeability of detector 34 has but little effect on the operation of a combustion system under closed loop control of excess oxygen. Primary importance is attached to sensor's dynamic performance in regard to stability, resolution and speed of response. For example, an optimal measurement of oxygen demand, achieving 0.1% resolution, may require a detection uncertainty not exceeding 50 parts per million, when expressed as the sum of sensor drift, plus sensitivity, on a volumetric basis.

(d) The feedback control of hydrogen generating current operates to maintain the residual concentration of oxygen in the flue gas at a fixed level. The setpoint for oxygen is desirably established to maximize the completeness and linearity of combustion. A further consideration involves selection of the oxygen setpoint at an above zero value providing adequate signal and control headroom.

Each unit of current is equated with a known amount of titrant through the Faraday Law, each milliampere yielding 6.954 microliters of hydrogen (at standard temperature and pressure), or proportionately equivalent oxygen. Thus gas' oxygen demand for complete combustion is known from the difference between total oxygen consumed (from fixed air supply) and the amount accounted for by titrant. Gross calorific content of gas per standard unit volume is computed from gas' oxygen demand per like unit of gas volume by application of the proportionality constant appropriate to the desired units. In one common system of units, this factor is 506.2 British thermal units per standard cubic foot of gas.

Moisture removal may be practiced in the titrant generator 39 since rapid gas evolution results in substantial spray, in addition to water vapor saturation of the electrolysis product. Downstream condensate can cause titrant delivery disruption, as well as degradation of combustion efficiency. Solid state thermoelectric devices, often referred to as Peltier modules, may be employed to create a miniature refrigeration trap in order to strip excess moisture from titrant gas and return it to the main body of electrolyte.

The importance of minimizing titrant dead volume will be appreciated if the system's response to a dynamic change in electrolysis backpressure is considered. Dead volume represents titrant storage and has the effect of capacitance on delivery response time.

Use of an aqueous alkaline solution for the electrolyte makes the use of electrodes fabricated of non-precious metals possible. This is an important consideration because appreciable electrode surface areas are needed to generate the requisite titrant quantities at moderate voltages. Cathode 77 may be copper and anode 78 stainless steel. They have been found to have a useful life in excess of ten throusand ampere hours.

SUMMARY

The present invention provides a means to supply natural gas and air to chamber 29 in FIG. 1 at invariant volumetic rates. The air is delivered at a rate so that somewhat more oxygen is supplied than is needed for the complete burning of gas at any calorific value within a predetermined range.

In conjunction with oxygen sensor 34, control circuit 37 continuously determines the deviation of oxygen excess in combustion products from a setpoint excess. The circuit acts to minimize the deviation by regulating the electrolysis current to hydrogen generator 39. Evolved hydrogen through conduit 31 is added to the gas and air mixture prior to combustion. The generation current is, thus, a relatively accurate measure of oxygen in excess of gas combustion requirements. A pair of standard gases may conveniently establish apparatus calibration if their known oxygen demands and corresponding calorific values encompass its measurement range. Thus, the relative hydrogen generation current required to maintain setpoint quantifies natural gas' oxygen demand ratio and, hence, its gross calorific value.

What is claimed is:

1. Apparatus for the automatic and continuous determination of a molar ratio of oxygen to a gas for stoichiometrically complete combustion, comprising: first means to produce a flow of a combustible gas at an invariant, standard volumetric rate; second means to produce a flow of air at an invariant, standard volumetric rate; electrolysis means having an electrical input current to produce a variable titrant flow; third means of combusting said gas, said air and said titrant in a manner such that combustion is substantially complete; a sensor providing electrical signals corresponding to the level of oxygen after combustion; electronic control circuitry connected from said sensor regulating titrant to maintain a predetermined oxygen excess; and utilization means to produce an output which is a linear function of said current.

2. Apparatus according to claim 1, in which said ratio is related to said gas' gross calorific content on a standard volumetric basis.

3. Apparatus according to claim 1, wherein said electrolysis means produces a titrant which is one of the gases hydrogen and oxygen, said electrolysis means including a partitioned electrolysis cell isolating products evolved at anode and cathode while providing for ion exchange, an aqueous, alkaline electrolyte solution, a means inhibiting said electrolyte circulation or displacement between anode and cathode chambers, a pair of common metal electrodes, and a moisture condensing and removal means for drying evolved titrant.

4. Apparatus according to claim 1, wherein said third means of combustion comprise a mixture delivery tube; a burner head constructed with an open-topped cup in a manner such that combustion proceeds within the interior of said cup, said cup being enclosed and supported by said delivery tube, a flue stack, said stack being sealably mounted to said mixture delivery tube at a point preceding the flame zone, said stack serving to remove combustion products, and preserve their integrity during delivery to sensor; and insulation means about the flue stack in the flame zone region.

5. Apparatus according to claim 4, wherein said burner cup has a plurality of sidewall holes extending therethrough, a space being defined by the cup's external wall and the internal wall of the delivery tube, said holes being oriented angularly so that said mixture acquires a uniformly high swirl motion in entering cup.

6. Apparatus according to claim 1, wherein said second means produces air that is filtered, compressed, dried and precisely regulated in pressure, said air being supplied at a rate to provide sonic flow, said second means including a critical orifice to fix the air flow at an invariant standard volumetric rate, constant temperature means maintaining said orifice and supply air in thermal equilibrium.

7. Apparatus according to claim 6, wherein said first means includes a pressure regulated source of said gas; said second means producing a flow of pilot air; and a positive displacement metering pump having a plurality of diaphragm chambers in thermal equilibrium; a diaphragm for each chamber, said diaphragms being subject to displacement; and valving means actuable synchronously to alternately admit said gas to one said chamber, to displace a volume of air to be vented, and to simultaneously admit said pilot air to another said chamber, the displaced volume of said gas to be delivered.

8. A calorimeter comprising: first means for producing air at a constant molar rate; second means for producing natural gas at a constant molar rate; third means for producing gas at a variable rate; fourth means to combine said air and said natural gas and said hydrogen gas at the same temperature and pressure, the uncombined mixture being such that the oxygen therein is at least equal to that required for complete combustion of said natural gas when it has a predetermined number of thermal units per unit weight; a combustion chamber having one inlet and one outlet; means to introduce said mixture into said inlet, said chamber holding said natural gas and said hydrogen in a condition burning in the presence of said air; an oxygen sensor connected from said combustion chamber outlet, said oxygen sensor having an electrical output, said oxygen sensor including means to produce an electrical signal on the said output lead thereof directly proportional to the oxygen remaining after combustion; and proportioning means connected from said oxygen sensor to said third means to cause the latter to generate hydrogen at a mass flow rate tending to cause the oxygen mass flow rate to said oxygen sensor to be reduced substantially to zero.

9. The invention according to claim 8, wherein said third means includes means for producing hydrogen by electrolysis, said proportioning means supplying an electric current to said third means directly proportional to the amount of hydrogen generated.

10. The invention according to claim 9, wherein utilization means are connected from said proportioning means.

11. The invention according to claim 10, wherein said utilization means includes an electrical instrument having means to indicate the heat content of said natural gas, the rate of change of the magnitude of said indication being directly proportional to the rate of change of said electric current.

12. The invention according to claim 11, wherein the oxygen introduced to said combustion chamber exceeds that required for complete combustion of said natural gas by about three percent when the calorific value of said natural gas is a maximum.

* * * * *